US006666844B1

(12) United States Patent
Igo et al.

(10) Patent No.: US 6,666,844 B1
(45) Date of Patent: Dec. 23, 2003

(54) METHOD AND APPARATUS FOR ACCESSING THE PERICARDIAL SPACE

(76) Inventors: Stephen R. Igo, 1302 Marina Bay Dr., #209A, Clear Lake Shores, TX (US) 77565; James W. Meador, 4715 Oakshire Dr., Houston, TX (US) 77027; Ruben Trono, 823 Christopher St., Marion, OH (US) 43302

( * ) Notice: Subject to any disclaimer, the term of this patent is extended or adjusted under 35 U.S.C. 154(b) by 0 days.

(21) Appl. No.: 09/625,900

(22) Filed: Jul. 26, 2000

Related U.S. Application Data

(60) Continuation of application No. 09/158,024, filed on Sep. 21, 1998, now Pat. No. 6,162,195, which is a division of application No. 08/484,299, filed on Jun. 7, 1995, now Pat. No. 5,827,216.

(51) Int. Cl.[7] .................................................. A61M 5/00
(52) U.S. Cl. .................. 604/115; 604/164.04; 604/174; 604/176
(58) Field of Search ................................ 604/21–22, 53, 604/158, 159, 164–165, 264, 268, 272, 176; 607/116, 119, 122–123, 125–6, 129–131

(56) References Cited

U.S. PATENT DOCUMENTS

| 3,630,207 A | * 12/1971 | Kahn et al. ............... 604/524 |
| 3,804,097 A | 4/1974 | Rudie |
| 3,844,272 A | 10/1974 | Banko |
| 3,923,060 A | 12/1975 | Ellinwood, Jr. |
| 4,003,379 A | 1/1977 | Ellinwood, Jr. |
| 4,027,510 A | 6/1977 | Hiltebrandt |
| 4,230,123 A | 10/1980 | Hawkins, Jr. |
| 4,249,541 A | 2/1981 | Pratt |
| 4,464,171 A | 8/1984 | Garwin |
| 4,518,383 A | 5/1985 | Evans |
| 4,540,404 A | 9/1985 | Wolvek |
| 4,578,061 A | 3/1986 | Lemelson |
| 4,581,019 A | 4/1986 | Curelaru et al. |
| 4,620,547 A | 11/1986 | Boebel |
| 4,651,753 A | 3/1987 | Lifton |
| 4,656,999 A | 4/1987 | Storz |
| 4,662,870 A | 5/1987 | Augustine et al. |
| 4,759,348 A | 7/1988 | Cawood |
| 4,763,667 A | 8/1988 | Manzo |
| 4,791,937 A | 12/1988 | Wang |
| 4,940,468 A | 7/1990 | Petillo |
| 4,961,729 A | 10/1990 | Vaillancourt |
| 4,991,578 A | 2/1991 | Cohen |

(List continued on next page.)

FOREIGN PATENT DOCUMENTS

| EP | 0 417 031 A2 | 3/1991 |
| WO | WO 96/40368 | 12/1996 |
| WO | WO 97/16170 | 5/1997 |
| WO | WO 98/05289 | 2/1998 |

Primary Examiner—Brian L. Casler
Assistant Examiner—Catherine Serke
(74) Attorney, Agent, or Firm—Beck & Tysver, P.L.L.C.

(57) ABSTRACT

A pericardiocentesis apparatus and method for accessing the pericardial space. The invention consists of inserting a percutaneous tube whose tip has a hole which is positioned over and contacts the anterior pericardium. Introducing a vacuum within said tube forms a pericardial bleb within that hole. A guided needle within the tube is advanced to puncture the pericardial bleb while avoiding contact with the epicardium. A hollow filament or electrocardial lead or flexible guide wire within said needle can then be advanced into said pericardial cavity. The guide wire may be used to guide a intrapericardial catheter into the pericardial space for injection or infusion of selected therapeutic agents into the pericardial space to treat various heart and blood vessel diseases. Controlled drug release material(s) can be injected through said needle for the slow and/or sustained delivery of said therapeutic agents into said pericardial cavity.

9 Claims, 12 Drawing Sheets

U.S. PATENT DOCUMENTS

| | | |
|---|---|---|
| 5,019,039 A | 5/1991 | Anderson |
| 5,033,477 A | 7/1991 | Chin et al. |
| 5,053,044 A | 10/1991 | Mueller et al. |
| 5,071,412 A * | 12/1991 | Noda ......................... 604/176 |
| 5,071,428 A | 12/1991 | Chin et al. |
| RE34,086 E | 10/1992 | George |
| 5,213,570 A * | 5/1993 | VanDeripe ................... 604/28 |
| 5,235,966 A | 8/1993 | Jamner |
| 5,249,574 A | 10/1993 | Bush et al. |
| 5,269,326 A | 12/1993 | Verrier |
| 5,273,530 A | 12/1993 | del Cerro et al. |
| 5,281,230 A | 1/1994 | Heidmueller |
| 5,306,244 A | 4/1994 | Shiber |
| 5,324,254 A | 6/1994 | Phillips |
| 5,336,252 A * | 8/1994 | Cohen ......................... 606/129 |
| 5,342,296 A | 8/1994 | Persson et al. |
| 5,366,441 A | 11/1994 | Crawford |
| 5,366,463 A | 11/1994 | Ryan |
| 5,368,047 A | 11/1994 | Suzuki et al. |
| 5,373,855 A | 12/1994 | Skrabal et al. |
| 5,381,790 A | 1/1995 | Kanesaka |
| 5,385,156 A | 1/1995 | Oliva |
| 5,387,419 A | 2/1995 | Levy et al. |
| 5,392,765 A | 2/1995 | Muller |
| 5,395,312 A | 3/1995 | Desai |
| 5,409,457 A | 4/1995 | del Cerro et al. |
| 5,634,895 A | 6/1997 | Igo et al. |
| 5,681,278 A | 10/1997 | Igo et al. |
| 5,702,716 A | 12/1997 | Dunn et al. |
| 5,735,290 A | 4/1998 | Sterman et al. |
| 5,792,153 A * | 8/1998 | Swain et al. ................ 112/169 |
| 5,827,216 A * | 10/1998 | Igo et al. .................... 604/176 |
| 5,972,013 A * | 10/1999 | Schmidt ................ 604/164.01 |
| 6,162,195 A * | 12/2000 | Igo et al. ................ 604/164.01 |
| 6,206,004 B1 * | 3/2001 | Schmidt et al. ............. 128/898 |
| 6,231,518 B1 * | 5/2001 | Grabek et al. .............. 600/508 |

* cited by examiner

METHOD AND APPARATUS FOR ACCESSING THE PERICARDIAL SPACE

CROSS-REFERENCE TO RELATED APPLICATIONS

The present application is a continuation application of U.S. Ser. No. 9/158,024 filed Sep. 21, 1998, now U.S. Pat. No. 6,162,195, now which is a divisional application of U.S. Ser. No. 08/484,299 filed Jun. 7, 1995, now U.S. Pat. No. 5,827,216, which applications are incorporated herein by reference.

BACKGROUND OF THE INVENTION

This invention relates to methods and apparatus for accessing the pericardial space for medical treatment of the heart.

Knowledge of the pericardium dates back to the time of Galen (129–200 A.D.) the Greek physician and anatomist who gave the pericardium its name. The pericardial sac surrounds the heart like a glove enfolds a hand, and the pericardial space is naturally fluid-filled. The normal pericardium functions to prevent dilatation of the chambers of the heart, lubricates the surfaces of the heart, and maintains the heart in a fixed geometric position. It also provides a barrier to the spread of infection from adjacent structures in the chest, and prevents the adhesion of surrounding tissues to the heart. See generally, Holt J P: *The normal pericardium*, Amer J Cardiol 26:455,1970; Spodick D H: *Medical history of the pericardium*, Amer J Cardiol 26:447, 1970. The normal pericardial space is small in volume and the fluid film within it is too thin to functionally separate the heart from the pericardium. It has been observed that when fluid is injected into the pericardial space it accumulates in the atrioventricular and interventricular grooves, but not over the ventricular surfaces [Shabetai R: *Pericardial and cardiac pressure*, Circulation 77.1, 1988].

Pericardiocentesis, or puncture of the pericardium, heretofore has been indicated for (1) diagnosis of pericardial disease(s) by study of the pericardial fluid, (2) withdrawal of pericardial fluid for the treatment of acute cardiac tamponade, and (3) infusion of therapeutic agents for the treatment of malignant effusion or tumors. During 1994, it is estimated that approximately 12,000 pericardiocentesis procedures were performed in the United States and that less than 200 of these patients underwent therapy with the intrapericardial injection of drugs. At present, intrapericardial injection of drugs is clinically limited to the treatment of abnormal pericardial conditions and diseases, such as malignant or loculated pericardial effusions and tumors. Drugs that have been injected into the pericardial space include antibiotic (sclerosing) agents [Wei J, et al: *Recurrent cardiac tamponade and large pericardial effusions: Management with an indwelling pericardial catheter*, Amer J Cardiol 42:281,1978; Davis S, et al: *Intrapericardial tetracycline for the management of cardiac tamponade secondary to malignant pericardial effusion*, N Engl J Med 299:1113,1978; Shepherd F, et al: *Tetracycline sclerosis in the management of malignant pericardial effusion*, J Clin Oncol 3:1678,1985; Maher E, et al: *Intraperi-cardial instillation of bleomycin in malignant pericardial effusion*, Amer Heart J 11:613,1986; van der Gaast A, et al: *Intrapericardial instillation of bleomycin in management of malignant pericardial effusion*, Eur J Cancer Clin Oncol 25:1505,1989; Imamura T, et al: *Intrapericardial instillation of OK-432 for the management of malignant pericardial effusion*, Jpn J Med 28:62,1989, Cormican M, et al: *Intraperi-cardial bleomycin for the management of cardiac tamponade secondary to malignant pericardial effusion*, Brit Heart J 63:61,1990; Mitchell M, et al: *Multiple myeloma complicated by restrictive cardiomyopathy and cardiac tamponade*, Chest 103:946, 1993], antineoplastic drugs [Terpenning M, et al: *Intrapericardial nitrogen mustard with catheter drainage for the treatment of malignant effusions*, Proc Amer Assoc Cancer Res (abstr) 20:286,1979; Markman M, et al: *Intrapericardial instillation of cisplatin in a patient with a large malignant effusion*, Cancer Drug Delivery 1:49,1985; Figoli F, et al: *Pharmacokinetics of VM 26 given intrapericardially or intravenously in patients with malignant pericardial effusion*, Cancer Chemotherapy Pharmacol 20:239, 1987; Fiorentino M, et al: *Intrapericardial instillation of platin in malignant peri-cardial effusion*, Cancer 62:1904,1988], radioactive compound [Martini N, et al: *Intra-pericardial instillation of radioactive chronic phosphate in malignant pericardial effusion*, AJR 128:639,1977], and a fibrinolytic agent [Cross J, et al: *Use of streptokinase to aid in drainage of postoperative pericardial effusion*, Brit Heart J 62:217, 1989].

Intrapericardial drug delivery has not been clinically utilized for heart-specific treatments where pericardial pathology is normal, because the pericardial space is normally small and very difficult to access without invasive surgery or risk of cardiac injury by standard needle pericardiocentesis techniques. The pericardiocentesis procedure is carried out by experienced personnel in the cardiac catheterization laboratory, with equipment for fluoroscopy and monitoring of the electrocardiogram. Electrocardiographic monitoring of the procedure using the pericardial needle as an electrode is commonly employed [Bishop L H, et al. *The electrocardiogram as a safeguard in pericardiocentesis*, JAMA 162:264,1956; Neill J R, et al: *A pericardiocentesis electrode*, N Engl J Med 264:711,1961; Gotsman MS, et al: *A pericardiocentesis electrode needle*, Br Heart J 28:566, 1966; Kerber R E, et al: *Electrocardiographic indications of atrial puncture during pericardiocentesis*, NEngl JMed 282:1142,1970]. An echocardiographic transducer with a central lumen has also been used to guide the pericardiocentesis needle [Goldberg B B, et al: *Ultrasonically guided pericardiocentesis*, Amer J Cardiol 31:490,1973]. Complications associated with needle pericardiocentesis include laceration of a coronary artery or the right ventricle, perforation of the right atrium or ventricle, puncture of the stomach or colon, pneumothorax, arrhythmia, tamponade, hypotension, ventricular fibrillation, and death. The complication rates for needle pericardiocentesis are increased in situations where the pericardial space and fluid effusion volume is small (i.e., the pericardial size is more like normal).

Chin et al have described a method and apparatus for accessing the pericardial space for the insertion of implantable defibrillation leads [US. Pat. No. 5,071,428]. The method required gripping the pericardium with a forceps device and cutting the pericardium with a scalpel (pericardiotomy) under direct vision through a subxiphoid surgical incision.

A method for the intrapericardial injection of angiogenic agents has been reported [Uchida Y, et al: *Angiogenic therapy of acute myocardial infarction by intrapericardial injection of basic fibroblast growth factor and heparan sulfate*, Circulation AHA Abstracts—1994]. While the method was not described in detail, it generally involved the percutaneous transcatheter bolus injection of drugs into the pericardial cavity via the right atrium. The major limitation of this method is that the right atrial wall is crossed which could lead to bleeding into the pericardial space. In addition, the method involved the bolus injection of drugs rather than long-term delivery via a catheter or controlled release material.

SUMMARY OF THE INVENTION

A principal object of the invention is to provide a method and apparatus for accessing the pericardial space without invasive surgery and to reduce the risk of injury to the heart during pericardial catheterization.

A more specific object of the invention is to provide an apparatus with the means to create a needle puncture through the wall of the pericardium without puncture of the heart.

A further object of the invention is to provide an apparatus with a lumen to be used for the introduction of other elements and materials into the pericardium for site-specific drug delivery to the heart and coronary arteries, or the introduction of implantable defibrillator or other cardioregulatory electrodes into the pericardial space.

Still another object of the invention is to provide a method for advancing a catheter into the pericardial space for the withdrawal of pericardial fluid and/or the intrapericardial injection or infusion of bioactive therapeutic agents to treat diseases of the heart and coronary arteries.

Yet another object of the invention is to provide an apparatus having a simple mode of operation which may be used to pass a guide wire and catheter into the pericardial space without the need for invasive surgery.

The present invention provides apparatus and method for nonsurgical access to the pericardial space through a needle puncture of the anterior pericardium (pericardiocentesis) in a manner reducing risk of injury to the heart, provides a lumen for introduction of substances into the pericardial space through the pierced pericardium, and allows introduction of a catheter into the pericardial space so accessed, thereby to enable the withdrawal of pericardial fluid and/or the intrapericardial injection or infusion of bioactive therapeutic agents to treat diseases of the heart and coronary arteries in a site specific manner, or to allow the introduction of implantable defibrillator electrodes into the pericardial space.

An apparatus of the present invention for percutaneously accessing the intrapericardial space comprises an elongated outer tubular body having a closed distal end, an aperture in a sidewall adjacent the closed end, and a proximal portion for applying a vacuum thereto. An elongated inner tubular body has a distal end sealingly extending into the outer tubular body from a proximal end external to the outer tubular body, creating a first passage between the first and inner tubular bodies. A piercing body is disposed in a distal portion of the outer tubular body adjacent the aperture. The piercing body has a sharp distal end and a lumen extending through it from a proximal end of it to a sidewall opening in it adjacent such sharp distal end. The proximal end of the piercing body is connected to the distal end of the inner tubular body, thereby creating a conduit leading from outside the outer tubular body to the piercing body sidewall opening. The piercing body is longitudinally moveable in the outer tubular body to an extent permitting the distal end of the piercing body to traverse the aperture of the outer tubular body and appose the sidewall opening of the piercing body and the aperture of the outer tubular body. Means providing a passage are laterally adjacent the piercing body for permitting flow communication from the aperture of the outer tubular body to the passage between the tubular bodies, under influence of an applied vacuum, regardless of the longitudinal location of the piercing body in the distal portion of the outer tubular body.

The invention further constitutes a method for accessing a pericardial space, which comprises percutaneously inserting the distal portion of an elongated outer tubular body containing an aperture in a sidewall adjacent the distal end, locating such distal portion over the pericardium substantially parallel thereto with the aperture facing the pericardium surface, applying a vacuum to the tubular body remotely from the distal portion to draw a portion of the pericardium away from the surface of the heart into the aperture in a capture position, advancing a piercing element contained in the tubular body adjacent the aperture in a direction substantially parallel to the heart to pierce the portion of the pericardium captured in the opening, and retracting the piercing element to leave a hole in the pericardium.

The method of this invention further includes delivering a substance through the tubular body and into the pericardial space through the hole created in the pericardium. The substance suitably may be formed or formless. Suitably a formed substance is the distal portion of a filament. The filament may be electro- or photo-conductive, for example, a defibrillator electrode; it may be solid, such as a guidewire; or it may be hollow, such as a catheter. Alternatively the substance may be formless, such as a liquid, paste or gel, and may be bioactive as a cardiovascular drug.

Where the substance is a filament, the method further comprises withdrawing the tubular body and the piercing body over the filament, leaving the filament distal portion in place in the pericardial space with a proximal portion inclusive of the proximal end of the filament remaining external to the body of the patient. Where the filament is electro- or photo-conductive, the invention further comprises accessing the proximal portion of the filament to regulate the heart. Where the filament is hollow, this method thereby provides an indwelling catheter to the pericardial space.

This invention suitably employs an elongated inner tubular body having a distal end sealingly extending into the percutaneously inserted outer tubular body from a proximal end external to the outer tubular body. The piercing element suitably comprises a body having a sharp distal end and a lumen extending therethrough from a proximal end thereof to a sidewall opening therein adjacent such sharp distal end, the proximal end of the piercing body being connected to the distal end of the inner tubular body, thereby creating a conduit leading from externally of the outer tubular body to the piercing body sidewall opening, the piercing body being longitudinally moveable in the outer tubular body to an extent permitting the distal end thereof to traverse the aperture and appose the piercing body sidewall opening and the aperture. In this embodiment, the substance is delivered through the so provided conduit into the pericardial space through the hole created in the pericardium.

In this latter aspect, where the substance is the distal portion of a filament, the step of delivering comprises advancing a filament distal portion through the inner tubular body and through the pericardium portal into the pericardial space. Where the filament is a guidewire, the method of this invention further comprises withdrawing the first and inner tubular bodies and the piercing body over the guidewire, leaving the distal portion of said guidewire in place in the pericardial space, advancing the leading end of a catheter over said guidewire into said pericardial space, and then withdrawing said guidewire to leave said catheter end in said pericardial space. A bioactive substance may then be delivered into the pericardial space through this catheter.

Preferably the distal end of the tubular body is radio-opaque. Suitably the apparatus further comprises an electroconductive terminal adjacent said aperture and a terminal lead electroconductively communicating said terminal exteriorly of outer tubular body remotely from said distal end of said outer tubular body.

The nature, objects, and advantages of the present invention will become more apparent to those skilled in the art when viewed in light of the following detailed description and accompanying drawings.

BRIEF DESCRIPTION OF THE DRAWINGS

FIG. 8 is a longitudinal, centerline sectional, side schematic view of the distal end of the invention illustrating its position over the anterior surface of the pericardium.

FIG. 9 is a longitudinal, centerline sectional, side schematic view of the distal end of the invention illustrating capture of the pericardium with suction and formation of the pericardial bleb.

FIG. 10 is a longitudinal, centerline sectional, side schematic view of the distal end of the invention illustrating the needle in the fully advanced (extended) position with puncture of the pericardial bleb.

FIG. 11 is a longitudinal, centerline sectional, side schematic view of the distal end of the invention illustrating insertion of the guide wire through the needle into the pericardial space.

FIG. 12 is a side schematic view of the pericardium after removal of the invention illustrating the intrapericardial guide wire.

DETAILED DESCRIPTION OF THE PREFERRED EMBODIMENTS

Figure 1:
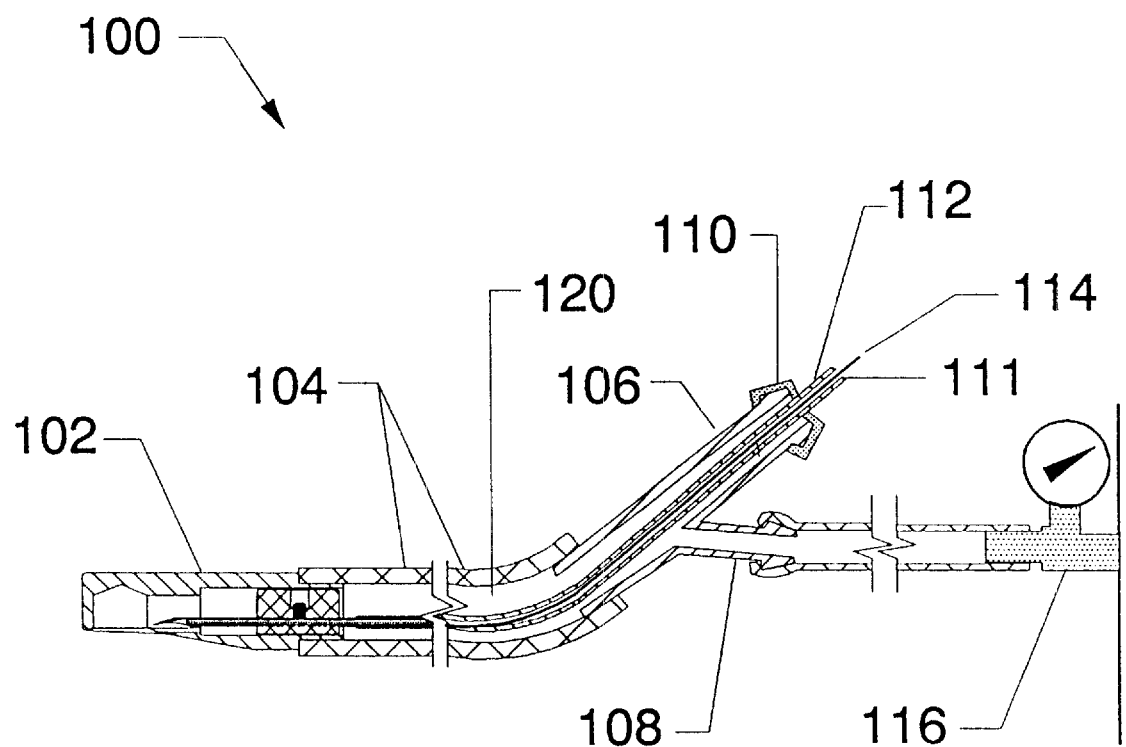
FIG. 1 is a longitudinal, centerline sectional, sidegraphical outline or schematic view of the invention illustrating a preferred embodiment of the pericardiocentesis apparatus for nonsurgical intrapericardial access.

Referring to FIG. 1, an introducer apparatus 100 for percutaneously accessing the intrapericardial space and constructed in accordance with this invention, comprises a distal end portion 102 which is attached to and may be considered a distal extension of first elongate outer tubular body 104 which in turn is attached to a connector portion 106, which may be considered a proximal extension of tubular body 104. Connector portion 106 has a side branch 108 which in turn is connected to a vacuum supply 116. A second or inner elongate tubular body 112 having a distal end 111 and a proximal end 113 extends into first or outer tubular body 104 including connector portion 106 from outside outer tubular body 104, creating a passage 120 between first and inner tubular bodies 104 and 112. Passage 120 is an annulus where first and inner tubular bodies 104 and 112 are circular in cross section. At the end of connector 106 is a seal or gasket 110 which seals passage 120 inside of the tubular body 104 and connector portion 106 from ambient pressure while still permitting inner tubular body 112 to move in and out of connector portion 106. Loaded within tubular body 112 is a guide wire 114.

Figure 2:
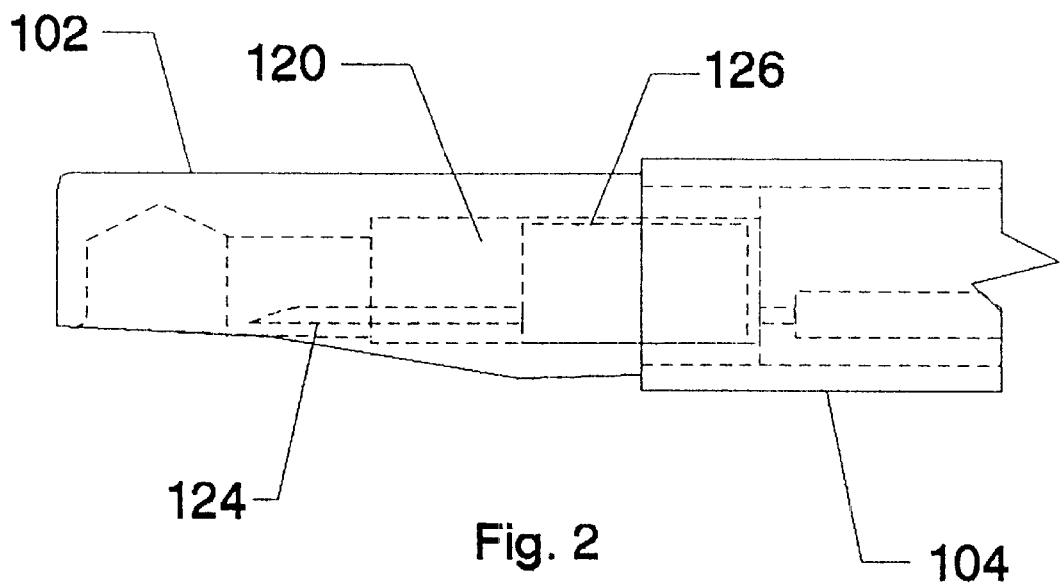
FIG. 2 is a side schematic view of the distal end portion of the invention.
Figure 3:
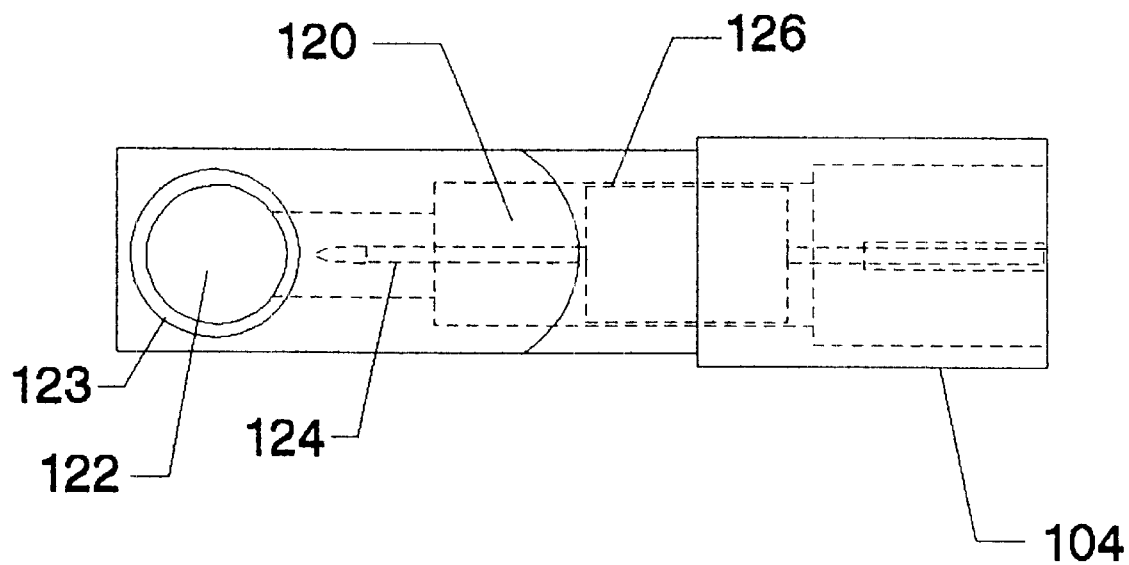
FIG. 3 is a bottom schematic view of the distal end portion of the invention.
Figure 4:
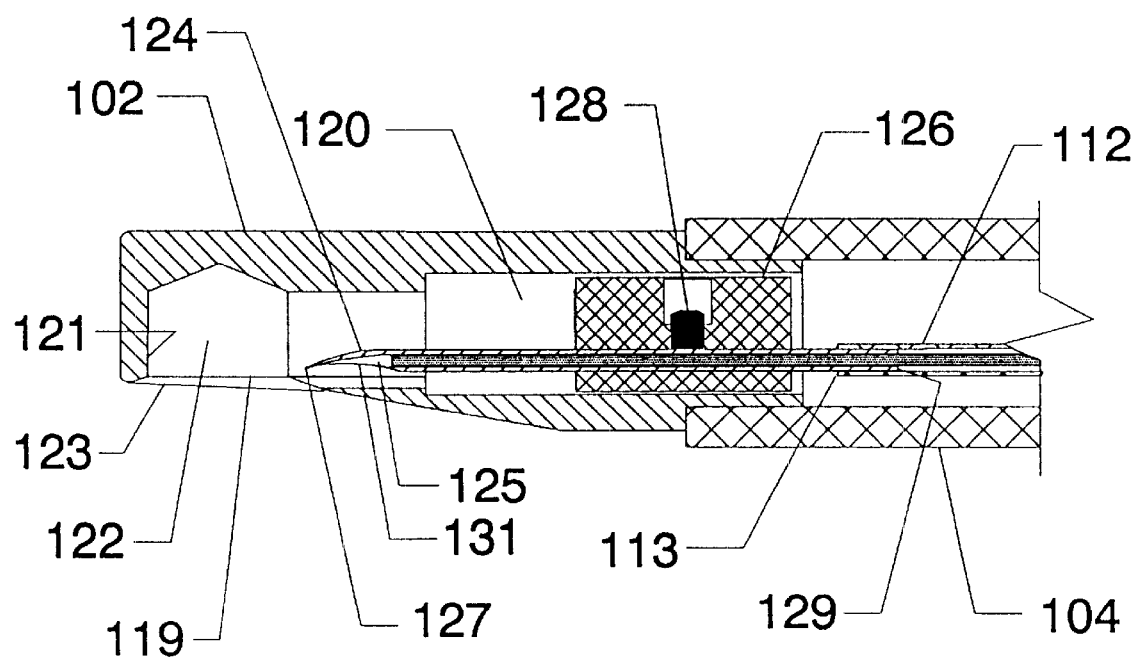
FIG. 4 is a longitudinal, centerline sectional, side schematic view of the distal end of the invention.

The distal end portion 102 is illustrated in FIG. 2 with a close-up side-view. The bottom-view of FIG. 2 is illustrated in FIG. 3. A centerline sectional side-view of FIG. 2 is illustrated in FIG. 4. The distal end portion 102 of introducer apparatus 100 is radio-opaque, rigid, and contains an axial passage 120 which is part of a continuous passage 120 in segments 106 and 108 of outer body 104. The passage 120 in distal portion 102 terminates axially at a closure or end portion 121. A radial bore 122 in tubular body sidewall 119 adjacent closure end 121 intersects, suitably orthogonally, passage 120 and creates a cavity at 122 entered by aperture 123. A needle carrier block 126 is arranged and moveable longitudinally in passage 120 without occluding flow communication of fluid from aperture 123 toward branch 108 under influence of vacuum source 116. A needle 124 having an axial lumen 125 is carried in needle carrier 126 and attached to the needle carrier using a set screw 128. Needle 124 has a sharp leading or distal end 127 extending distally from carrier 126 and a trailing or proximal end 129 extending proximately from carrier 126. Needle 124 includes a sidewall lateral opening 131 adjacent sharp leading end 127 and positioned to be apposed to or alignedly juxtaposed over aperture 123 of radial bore 122 in passage 120 when needle carrier 126 is advanced in tubular body distal portion 102. At sidewall opening 131, lumen 125 accesses cavity 122 where piercing of pericardium 144 occurs. Distal end 111 of the second or inner tubular body 112 is axially connected to the trailing end 129 of needle 124, as shown in FIG. 2. This connection creates a conduit leading from externally of outer tubular body 104 through inner tubular body 112 and axial lumen 125 to needle sidewall opening 131. This enables access to the pericardial space through sidewall opening 131 after pericardium 144 is pierced. In FIGS. 1–11 this conduit is occupied by guidewire 114. The purpose of lumen 125 and the conduit leading through inner tube 112 is not to supply a vacuum to withdraw fluid. That is the purpose of passage 120, and passage 120 is much larger in cross section than lumen 125. Suitably the ratio of cross sectional areas of passage 120 to lumen 125 exceeds about 5 and may be up to about 200, more preferably from about 5 to about 100, the larger the number, the greater the vacuum force available. However, the vacuum force applied need be only sufficient to acquire and draw a bleb of pericardium into cavity 122 for piercing so that whatever is to be introduced through needle 124 can be delivered into the pericardial space so accessed.

Figure 5:
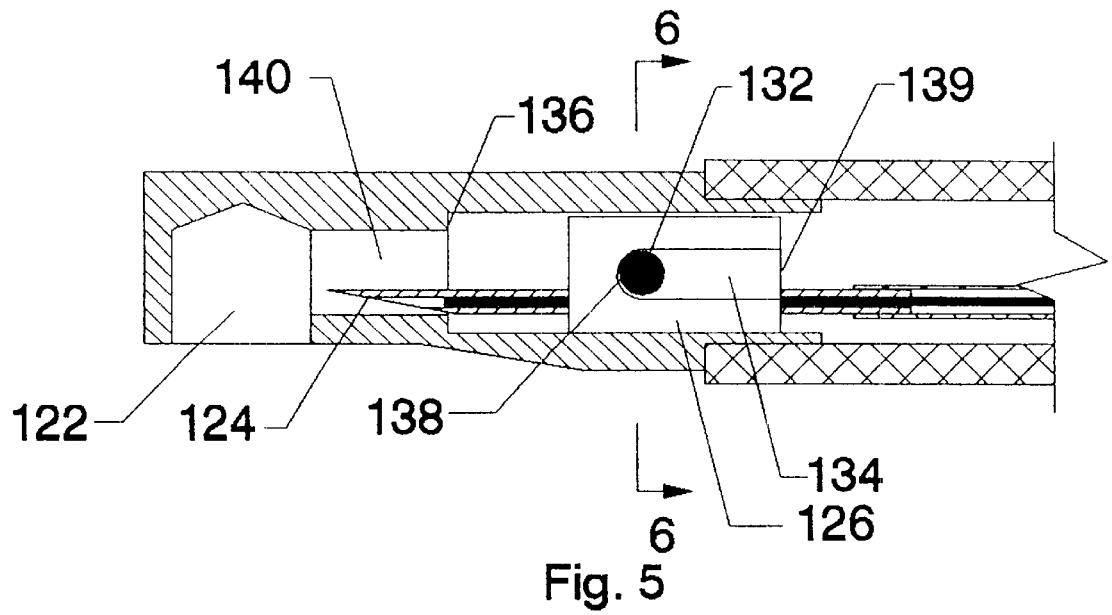
FIG. 5 is a longitudinal, centerline sectional, side schematic view of the distal end of the invention showing the needle in the fully retracted (sheathed) position.
Figure 6:
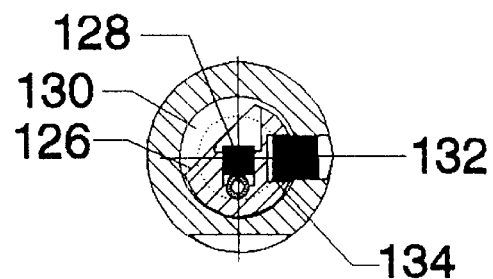
FIG. 6 is cross sectional view of FIG. 5, taken along the line 6—6 of FIG. 5.
Figure 7:
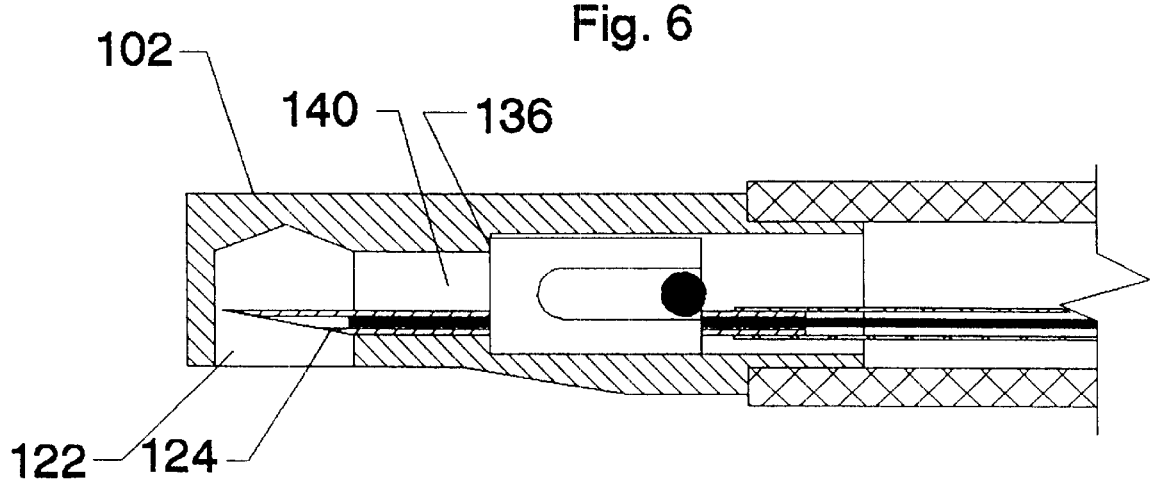
FIG. 7 is a longitudinal, centerline sectional, side schematic of the distal end of the invention showing the needle in the fully advanced (extended) position.

FIG. 5 is identical to FIG. 4 except that the needle carrier 126 and retaining screw 132 are not sectioned. Needle carrier 126, aside from providing a mechanism to mount needle 124 in proper alignment to a platform, also moves between two travel limiters arranged in tubular body distal portion 102 proximately of aperture 123 for limiting longitudinal movement of needle carrier 126 and hence needle 124 in tubular body distal portion 102 toward and away from closed distal end 121. Carrier 126 includes along an outer surface a longitudinal recess or groove 134 having a blind distal end 138 and an open proximal end 139. An interior protrusion such as a set screw 132 is mounted on tubular body 102 and extends transversely radially inward, as illustrated in FIG. 6, to protrude into groove 134. At the fully retracted or proximal position of needle holder 126, set screw 132 contacts the blind end 138 of groove 134. Another limiter comprises a constriction 140 at stop 136 in tubular body distal portion 102 distal to and narrower than needle carrier 126 that prevents further distal movement of needle holder 126 past the proximal portion of constriction 140 at stop 136, as shown in FIG. 7, fixing the fully extended or distal position of needle holder 126 in tubular body 102. As illustrated in FIGS. 5 and 7 the tip of needle 124 in the fully retracted position (FIG. 5) is limited by protrusion 132 and does not violate the boundary of bore 122. In the fully extended position (FIG. 7) limited by constriction 140 at stop 136, needle 124 extends significantly into bore 122.

Instead of this arrangement to control travel, both ends of groove 134 can be blind, with travel being limited by the stop; or a constriction can be furnished both distally and proximally of carrier 126. Indeed, the travel limiter for the fully extended position of needle 124 and needle carrier 126 suitably is provided by end closure 121 of distal portion 102 of outer tube 104. However, the embodiment illustrated is of simple construction and is satisfactory.

FIG. 6 is section 6—6 of FIG. 5. As seen in FIG. 6, needle carrier 126 is relieved in an upper of its body, providing a passage 130 laterally adjacent carrier 126 permitting flow communication from aperture 123 to the portion of passage 120 proximal of carrier 126, regardless of the longitudinal location of needle carrier 126 in the distal portion of outer tubular body 102. Subambient pressure provided by vacuum source 116 results in ambient gas flow from aperture 123 of the tubular body distal portion 102, through passage 120, around needle carrier 126 at passage 130, inside the annulus portion of passage 120 to side branch 108, to the vacuum source 116. Instead of relief of the outside periphery of carrier 126, other means of passage of fluid flow past carrier 126 may be employed, including longitudinal grooves along the periphery of carrier body 126 or separate channels external to the inner periphery of tubular body 104 accessed through openings into the passage 120 located beyond the limit of travel of carrier 126.

Second or inner tubular body 112, containing the guide wire 114, is sealed from subambient pressure via seal 110 on connector 106.

Figure 8:
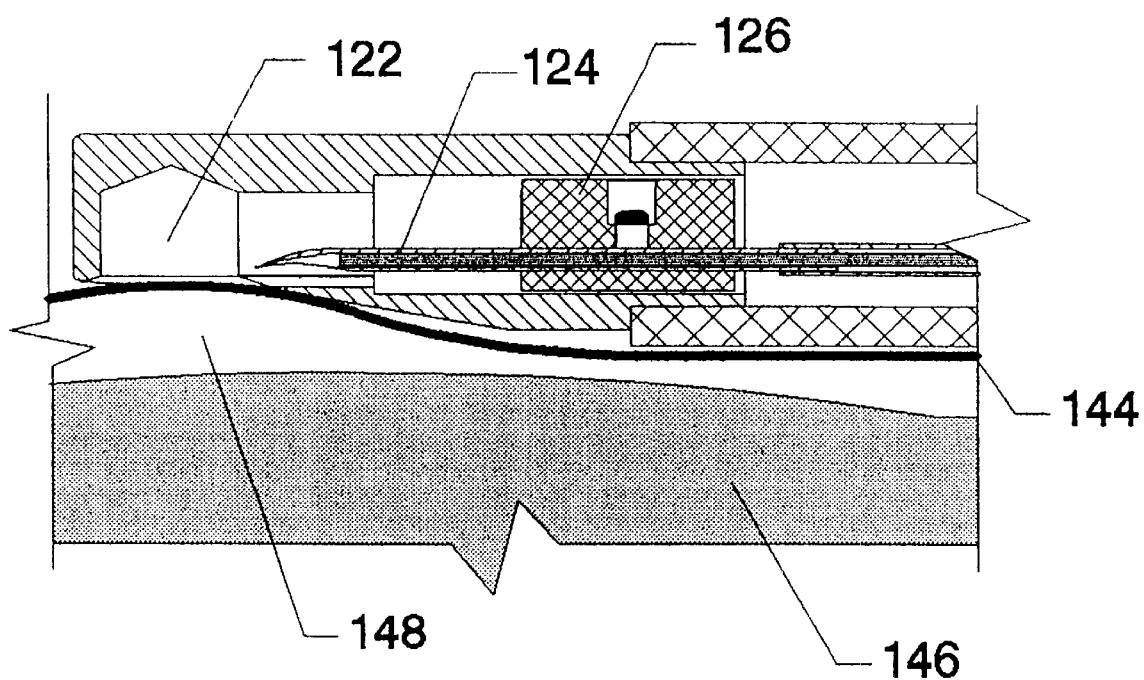
FIGS. 8 to 12 are longitudinal, centerline sectional, side schematic view of the distal end of the invention and the pericardium, sequentially illustrating the steps of practicing the present invention to first capture the pericardium, then puncture it with a needle (pericardiocentesis), and then insert a intrapericardial guide wire.
Figure 9:
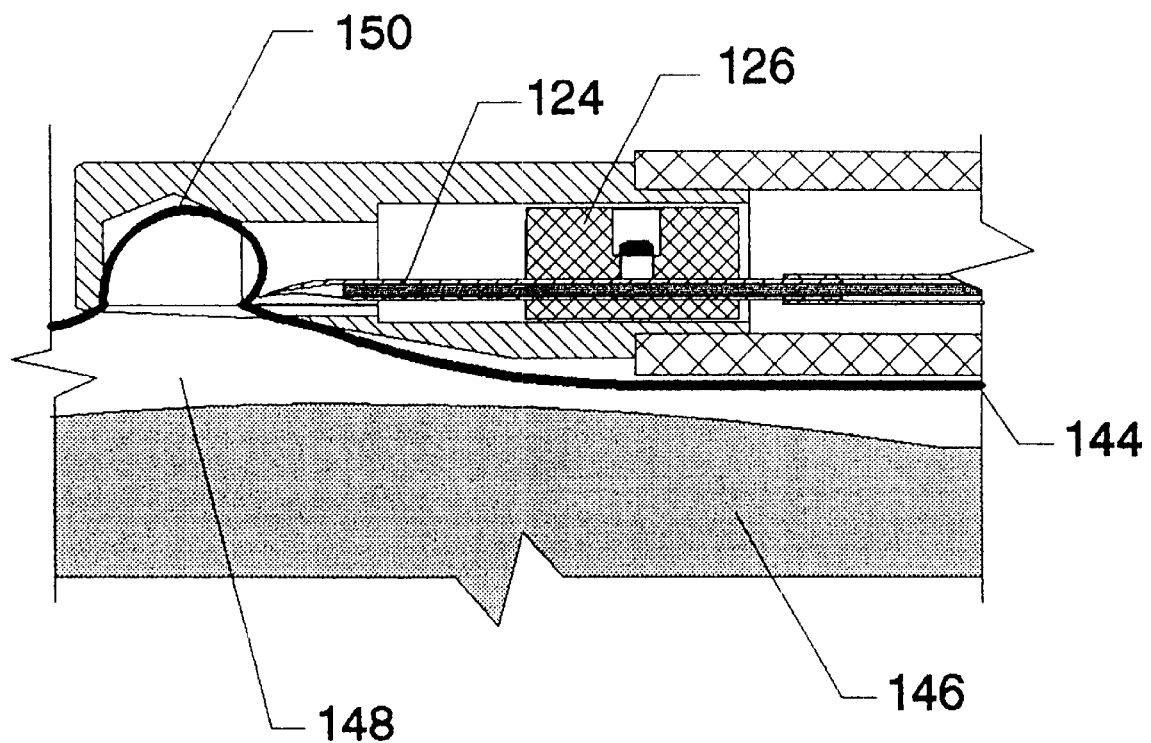
Figure 10:
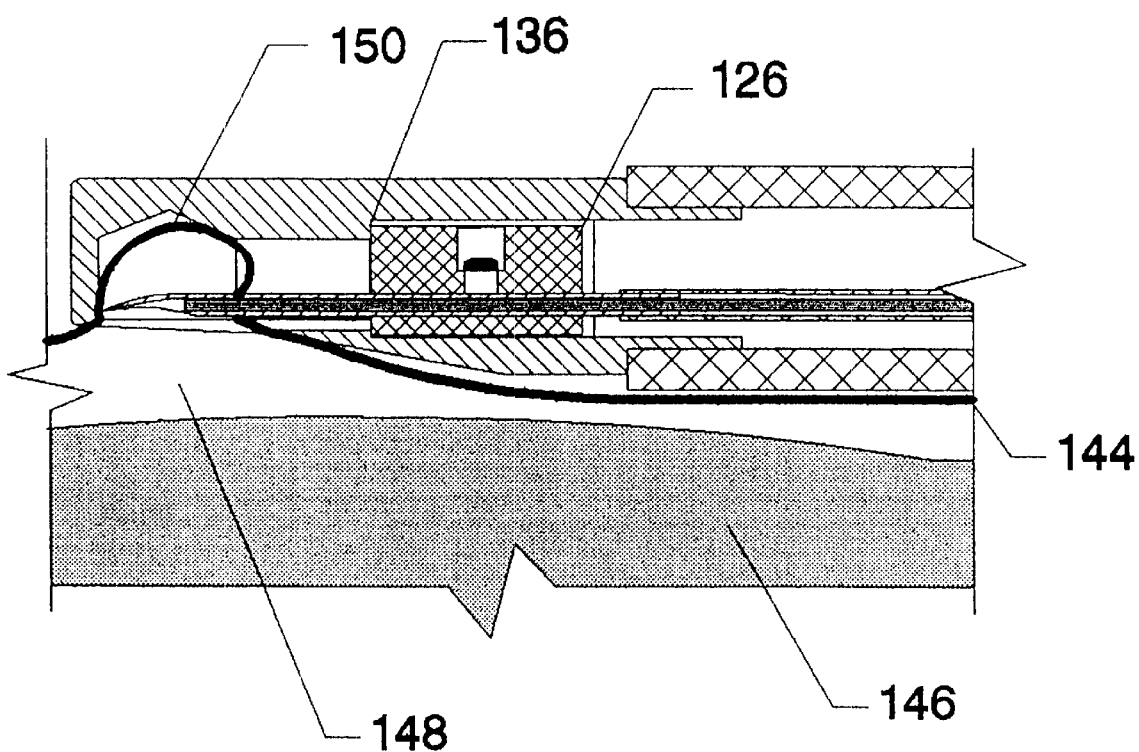

FIGS. 8 to 10 more particularly illustrate sequentially the inventive method for puncture of the pericardial wall. At the start of the procedure, a small subxiphoid incision is made in the skin. The method of the present invention for pericardiocentesis is then carried out through the following steps.

The tubular body device 104, with radio-opaque distal end 121, is inserted through the subxiphoid incision and advanced percutaneously, with the aid of fluoroscopy, over the diaphragm into the mediastinal space and is positioned so that the aperture 123 on the tubular body distal end 102 is over the anterior surface of the pericardial sac 144 (FIG. 8). Also shown in section is the wall of the ventricle 146 and the intrapericardial space 148.

Vacuum supply 116, connected to the branch portion 108 of outer tubular body 104, is then energized and air is evacuated from the distal portion 102 of tubular body 104 and the side opening 122 which is in contact with the pericardium 144. Once captured by suction, the pericardial sac 144 stretches to form a "bleb" 150 through aperture 123 into side opening 122 (FIG. 9).

After pericardial bleb 150 forms, as shown in FIG. 10, the operator may then advance needle 124, which is sheathed inside distal end 102 of outer tubular body 104 and aligned by movable needle holder 126. This is done by advancing inner tubular body 112 (FIG. 1) until needle holder 126 encounters stop 136. This forward movement causes needle 124 to sequentially prick and then puncture the pericardial bleb 150. The bleb 150 is pierced by needle 124 without contact or injury to the heart 146 since bleb 150 and needle 124 are isolated within cavity 122.

Figure 11:
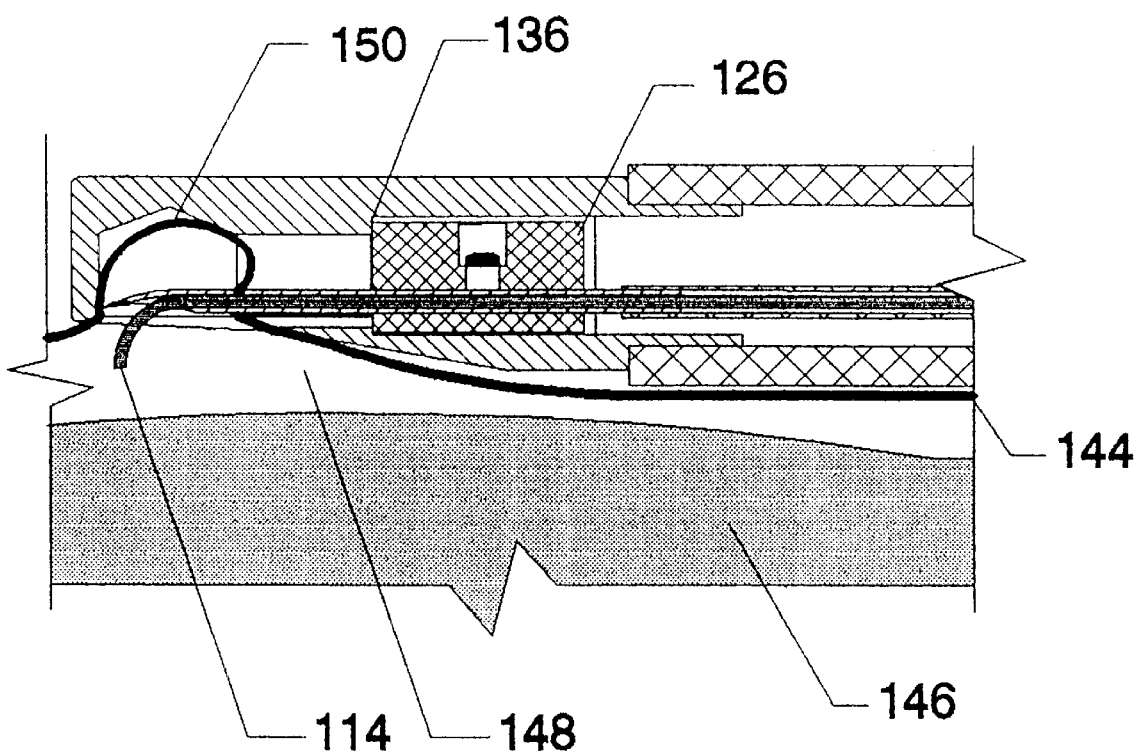
Figure 12:
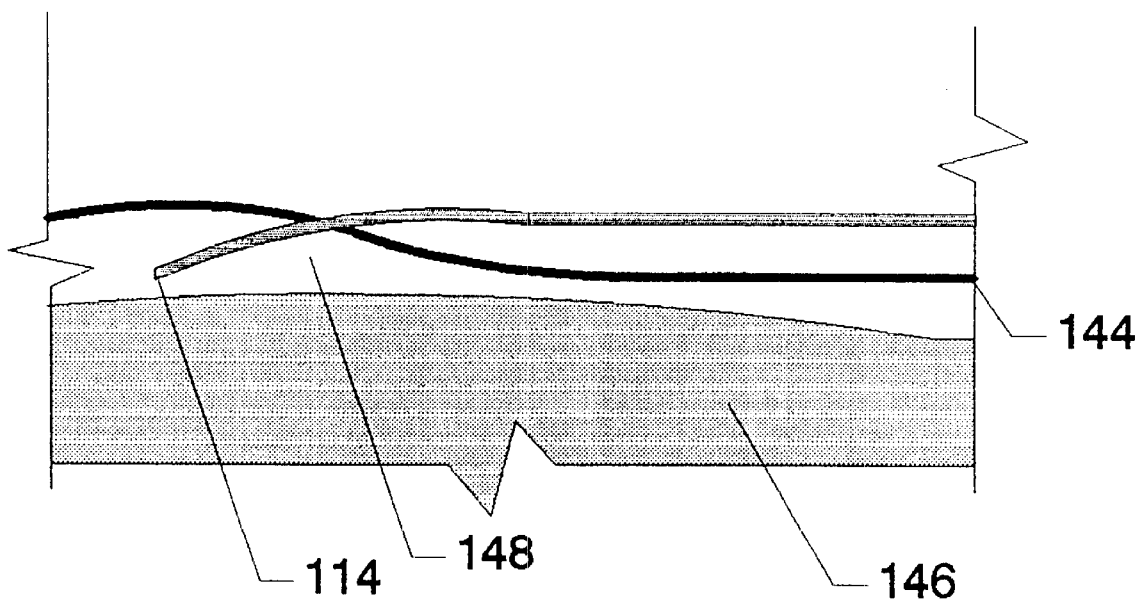

At this point the needle can be withdrawn to leave a hole in the pericardium for access in any of the ways generally described above. FIGS. 11–12 illustrate the aspect of the invention in which a guidewire is introduced into the pericardial space through the hole that was created in the pericardium.

After the hole is created in the pericardium, and with needle 124 in the fully advanced position at stop 136, the vacuum system is deactivated and a flexible guide wire 114 preloaded in needle 124 is then pushed through needle 124 into the pericardial space 148 between the heart 146 and pericardium 144 (FIG. 11). The needle is then retracted and the apparatus 100 is percutaneously removed from the patient leaving guide wire 114 in intrapericardial space 148 as illustrated in FIG. 12. Guide wire 114 facilitates access to the interior of the pericardium.

Figure 17:
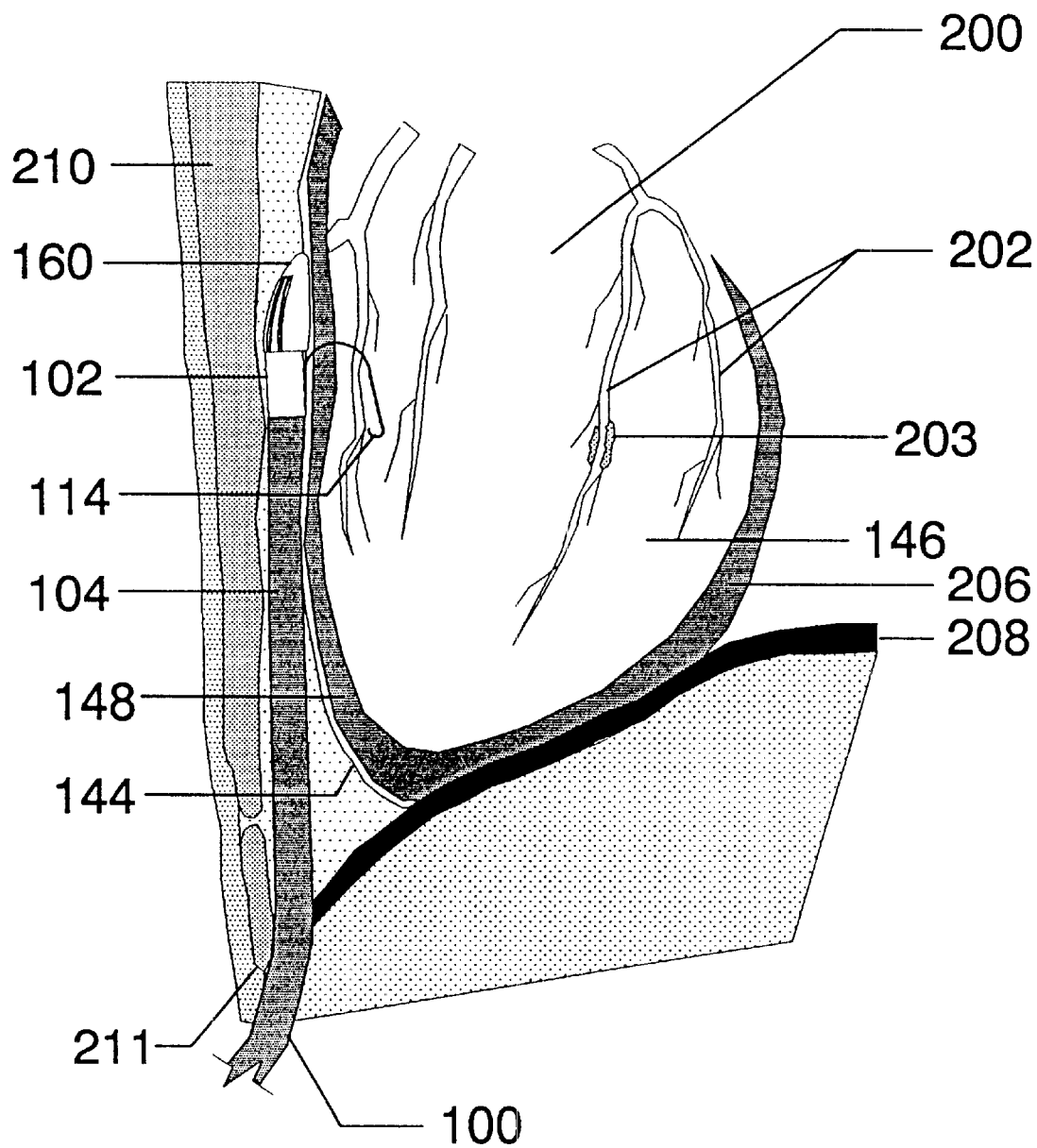
FIG. 17 is an illustration of the heart illustrating the placement of the pericardial access apparatus of the invention inserted subxiphoidally.

Referring now to FIG. 17, there is illustrated a human heart 200 and ventricle 146 showing the epicardial coronary arteries 202, the pericardial sac 144 enveloping heart 200, and pericardial space 148 containing pericardial fluid 206 bathing (exaggerated for purposes of illustration) heart 200 within pericardial sac 144. One of the coronary arteries 202 is indicated to be stenosed at 203. Below heart 200 is the diaphragm musculature 208. In the chest of the patient in front of heart 200 is the sternum 210 and the lower extension thereof called the xiphoid process 211. Shown percutaneously inserted below xiphoid process 211 is introducer 100 of this invention which has been advanced to a position over pericardium 144 with stabilizer portion 160 maintaining distal potion 102 of outer tube 104 substantially parallel to pericardium 204, assuring that aperture 123 and radial cavity 122 (not visible, but see FIGS. 8–11) are substantially normal to the pericardium for lifting a portion or bleb 150 of pericardium 144 into cavity 123 for needle piercing and hole creation substantially parallel to the heart to avoid risk of puncture of the heart. In FIG. 17, guidewire 114 has been advanced through the hole created in the pericardium.

After guidewire 114 has been advanced into the pericardial space, a catheter may then be percutaneously advanced over guide wire 114 into the pericardial space for the withdrawal of fluid, and/or the intrapericardial injection or infusion of therapeutic agents, or the intrapericardial insertion of implantable materials.

As mentioned before, the invention involves only in part the ability to introduce a guidewire and thereby a catheter into the pericardial space. The facility of the conduit provided by lumen 125 in flow communication with the lumen of inner tubular body 112 exiting outside outer tubular body 104 at its proximal end 111 at segment 106 gives a channel for fluids, pastes, gels, particles and solids passage directly to the pericardial space for administration of fluid or implant therapeutic agents to the heart or for implantation of electro- or photo-conductive cardioregulatory apparatus, suitably filamentary devices such as defibrillator electrodes, which, after withdrawal of apparatus 100, can be accessed outside the patients body and connected to body exterior devices for regulation or monitoring of the heart. Apparatus 100 may be supplied for use with this device channel empty, and when access is gained to pericardial space 146 as has been described, the agents to be delivered to the pericardial space can be pumped, injected or infused directly through this access channel to exit needle side opening 131 (still within pericardial space 146) and enter the pericardial space. Alternatively, apparatus 100 can be furnished preloaded with a filament in needle 125 which can be advanced into the pericardial space after it is accessed with apparatus 100. The filament may itself be hollow and serve as a catheter for in-dwelling administration of therapeutic agents after removal of apparatus 100. The filament can be solid, as in the instance of a guidewire or electro- or photo-conductive cardioregulation lead.

The present application is assigned to the assignee of U.S. patent application Ser. No. 08/264,458 filed Jun. 23, 1994, incorporated herein by reference, which describes a method of treating the coronary arteries of the heart that comprises application of therapeutic substances to the exterior surface of the heart. As already mentioned, fluid injected into the pericardial space accumulates in the atrioventricular and interventricular grooves. Since the epicardial coronary arteries are located in the grooves of the heart, a bioactive therapeutic substance delivered into the pericardial space through the methodology and device of this invention can accumulate and be concentrated over the coronary blood vessels. Intrapericardial drug delivery applications include injection/infusion of liquid drug preparations via a catheter placed according to this invention ("free drugs"), and delivery of constrained release materials for controlled drug release and time-based (long term) pharmacologic therapy, using the method and apparatus of this invention. Such constrained release materials suitably include implants and may comprise biopolymers, biodegradable fibers, liposomes, biodegradable polymeric microspheres, pastes, and gels. Thus this invention provides methods and means for accessing the pericardial space and delivery of a biodegradable drug loaded fiber which releases drug into the pericardial fluid for extended periods of time, for delivery of drug loaded liposomes or drug release microspheres (biodegradable polymer) to accumulate in the ventricular grooves and provide localized drug delivery to the coronary arteries, and for delivery of a drug loaded fibrin biopolymer or drug release gel which can be squeezed into the ventricular sulcus sites providing coronary artery site specific drug delivery. Depending on the viscosity of the substances used, regional site-specific treatment to a particular portion of the coronary circulation can be achieved by injecting the drug delivery material into the pericardium at a particular location using the apparatus of this invention.

Cardiovascular drugs for intrapericardial delivery can include vasodilator, antiplatelet, anticoagulant, thrombolytic, anti-inflammatory, antiarrhythmic, inotropic, antimitotic, angiogenic, antiatherogenic and gene therapy agents. Reference is made to co-pending U.S. patent application Ser. No. 08/264,458 filed Jun. 23, 1994 for a description of the methodology of treatment of cardiovascular disease by drugs placed in the pericardial space.

Figure 13:
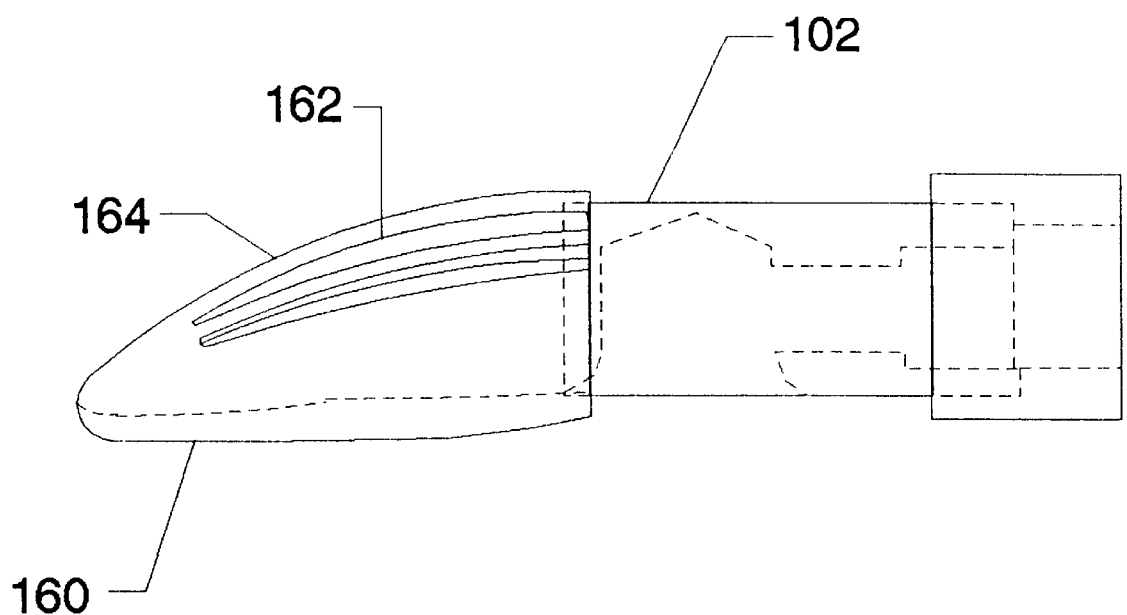
FIG. 13 is a side schematic view of the distal portion of the invention illustrating an embodiment of the intrapericardial access apparatus with a modified distal head.
Figure 14:
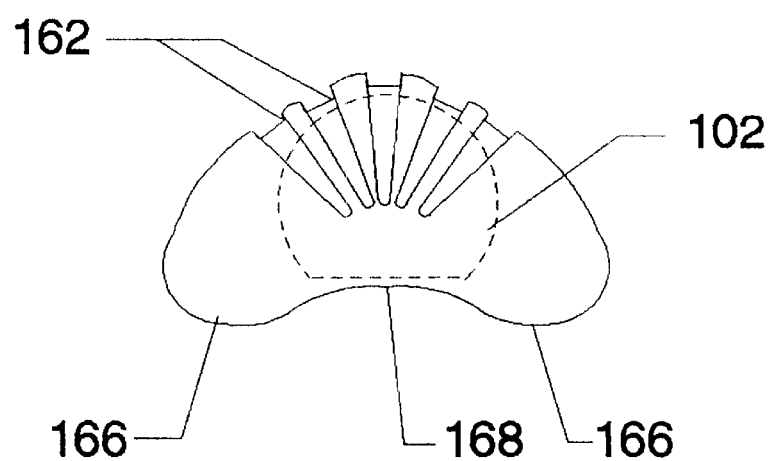
FIG. 14 is a front schematic view of the distal portion of the invention illustrating an embodiment of the intrapericardial access apparatus with a modified distal head.

FIG. 13 illustrates an embodiment of the present invention in which distal end 121 of the outer tubular body 104 comprises a stabilizer portion 160. FIG. 14 is a front view of FIG. 13. Stabilizer portion 160 is axially fixed to distal portion 102 of body 104, and is frontally ramped in a gently upward slope as indicated by 164, and narrows vertically from bottom to top as seen in FIG. 14. This frontal sloping eases entry under the sternum during insertion of the tubular body 104. Longitudinal grooves 162 along the upper surface of nose 160 help strip or otherwise remove fatty tissue on the pericardial surface away from the device, as well as provide a means of orienting the apparatus 100 to the surface of the pericardium. FIG. 14 indicates two downwardly shaped longitudinal nodes 166 which create a longitudinal concavity 168 between them. This concavity keeps the pericardium from bunching as the device is moved over it.

Figure 15:
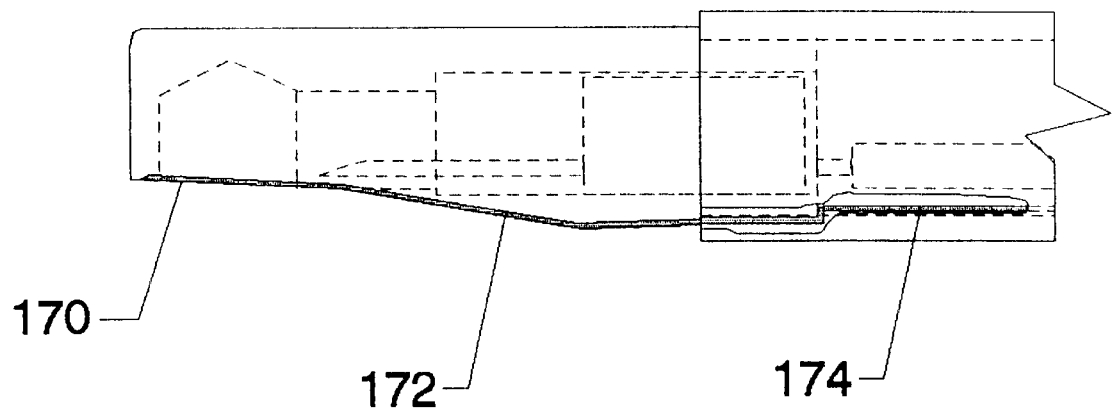
FIG. 15 is a side view of the distal portion of the invention illustrating an embodiment of the intrapericardial access apparatus with an electrode modification.
Figure 16:
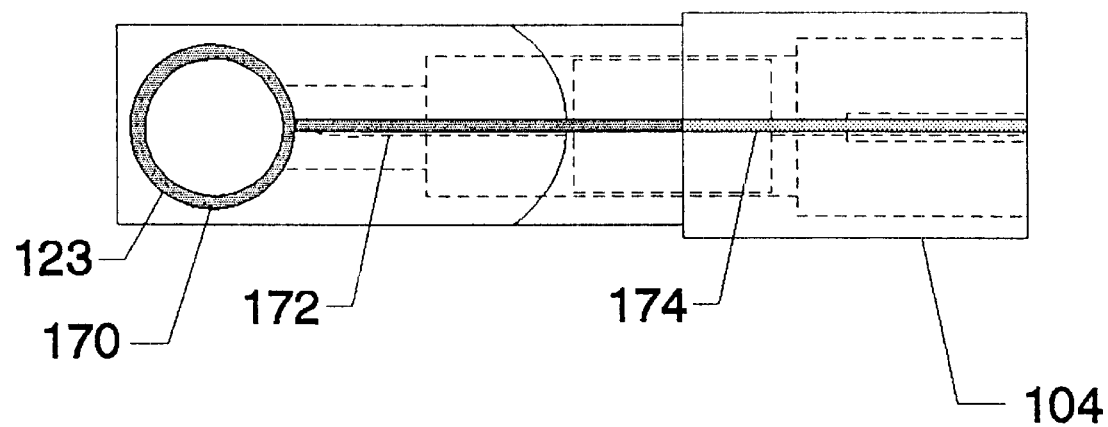
FIG. 16 is a bottom-view of the distal portion of the invention illustrating an embodiment of the intrapericardial access apparatus with an electrode modification.

FIG. 15 illustrates an embodiment of the present invention which includes an electroconductive terminal adjacent aperture 123 of outer tubular body distal portion 102 and a terminal lead electroconductively communicating exteriorly outer tubular body remote from distal portion 102. FIG. 16 is a bottom view of FIG. 15. A ring 170, which is electrically conductive around side opening entrance 123, communicates to an electrically conductive strip 172 which is a part of tubular body 102. FIG. 15 indicates part of the tubular body 104, cut away to show the addition of a wire 174 or equivalent which is attached to the electrically conductive material 172. The purpose of this device enhancement is to measure the electrocardiogram (EKG) signal from the heart 146 and pericardium 144, and transmit this signal back to the proximal end of the invention 100 where it is coupled to a EKG display monitor. Coupling of the invention 100 to a EKG monitor adds further information that the device is contacting the pericardium 144. Thus this invention further comprising monitoring the electrocardial signal of the heart to determine contact of aperture 123 of tubular body with the pericardium during said percutaneous insertion step.

The vacuum in tubular body 104 may also be monitored to detect a decrease in vacuum pressure marking capture of a bleb portion 150 of pericardium in aperture 123 and lateral opening 122.

From the foregoing detailed description, it is believed apparent that the present invention provides a method and apparatus for accessing the pericardial space by needle puncture (pericardiocentesis) without the need for invasive surgery and with a reduced risk of injury to the heart. It should be understood that the invention is not intended to be limited to the specifics of the described preferred embodiments, but is defined by the accompanying claims.

We claim:

1. A method of accessing the pericardial space within a patient's body, the method comprising:
   selecting an accessing instrument comprising:
   (i) a proximal end;
   (ii) a distal end;

(iii) a tube comprising a wall surrounding a lumen;
(iv) an opening in the wall near the distal end of the instrument, the opening being in fluid communication with the lumen; and
(v) a piercing element in the lumen, the piercing element being axially mobile within the lumen;

positioning the distal end of the instrument on the surface of an outer wall of the space;

drawing a planar portion of the outer wall of the space into the instrument opening using suction; and advancing the piercing element from a first position to a second position to pierce once, the portion of the outer wall of the space drawn into the instrument opening to position the piercing element within the space inside the outer wall and not through the wall.

2. A method of accessing the pericardial space within a patient's body, the method comprising:

selecting an accessing instrument comprising:
(i) a proximal end;
(ii) a distal end;
(iii) a tube comprising a wall surrounding a lumen;
(iv) an opening in the wall near the distal end of the instrument, the opening being in fluid communication with the lumen; and
(v) a piercing element in the lumen, the piercing element being axially mobile within the lumen;

positioning the distal end of the instrument on the surface of an outer wall of the space;

drawing a planar portion of the outer wall of the space into the instrument opening using suction; and advancing the piercing element from a first position to a second position to pierce once, the portion of the outer wall of the space drawn into the instrument opening to position the piercing element within the space inside the outer wall and not through the wall, and introducing a substance into the space through the piercing element wherein the substance comprises a drug.

3. The method of claim 2 wherein the drug is selected from the group consisting of antibiotics, antineoplastics, radioactives, fibrinolytics, and angiogenics.

4. The method of claim 2 wherein the drug is selected from the group consisting of vasodilators, antiplatelets, anticoagulants, thrombolytics, anti-inflammatories, antiarrthythmics, inotropics, antimitotics, angiogenics, antiatherogenics, and gene therapy agents.

5. A method of accessing the pericardial space within a patient's body, the method comprising:

selecting an accessing instrument comprising:
(i) a proximal end;
(ii) a distal end;
(iii) a tube comprising a wall surrounding a lumen;
(iv) an opening in the wall near the distal end of the instrument, the opening being in fluid communication with the lumen; and
(v) a piercing element in the lumen, the piercing element being axially mobile within the lumen;

positioning the distal end of the instrument on the surface of an outer wall of the space;

drawing a planar portion of the outer wall of the space into the instrument opening using suction; and advancing the piercing element from a first position to a second position to pierce once, the portion of the outer wall of the space drawn into the instrument opening to position the piercing element within the space inside the outer wall and not through the wall, and introducing a filament through the piercing element into the space.

6. The method of claim 5 wherein the filament is a guidewire.

7. The method of 6 further comprising withdrawing the instrument, leaving the guidewire in place, and advancing a catheter over the guidewire into the space.

8. The method of 7 further comprising introducing an electrode into the space through the catheter.

9. The method of claim 7 further comprising introducing a substance into the space through the catheter.

* * * * *